(12) United States Patent
Schroeder et al.

(10) Patent No.: US 7,642,395 B2
(45) Date of Patent: Jan. 5, 2010

(54) COMPOSITION AND WIPE FOR REDUCING VISCOSITY OF VISCOELASTIC BODILY FLUIDS

(75) Inventors: Karyn C. Schroeder, Neenah, WI (US); Candace D. Krautkramer, Neenah, WI (US); David W. Koenig, Menasha, WI (US); Douglas R. Hoffman, Oshkosh, WI (US); Katherine D. Stahl, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 287 days.

(21) Appl. No.: 11/025,643

(22) Filed: Dec. 28, 2004

(65) Prior Publication Data

US 2006/0140924 A1 Jun. 29, 2006

(51) Int. Cl.
*A61F 13/15* (2006.01)
*A61K 8/02* (2006.01)
*A01N 25/34* (2006.01)

(52) U.S. Cl. .................. 604/360; 604/359; 604/367; 604/364; 424/401; 424/404; 424/402

(58) Field of Classification Search ............. 604/360, 604/359, 367, 364; 424/401, 404, 402; 510/295, 510/405; 514/865, 847; 442/327
See application file for complete search history.

(56) References Cited

U.S. PATENT DOCUMENTS

| | | |
|---|---|---|
| 3,301,746 A | 1/1967 | Sanford et al. |
| 3,338,992 A | 8/1967 | Kinney |
| 3,341,394 A | 9/1967 | Kinney |
| 3,502,763 A | 3/1970 | Hartmann |
| 3,542,615 A | 11/1970 | Dobo et al. |
| 3,616,229 A | 10/1971 | Wildi et al. |
| 3,625,827 A | 12/1971 | Wildi et al. |
| 3,692,618 A | 9/1972 | Dorschner et al. |
| 3,802,817 A | 4/1974 | Matsuki et al. |
| 3,812,000 A | 5/1974 | Salvucci, Jr. et al. |
| 3,849,241 A | 11/1974 | Butin et al. |
| 3,974,025 A | 8/1976 | Ayers |
| 4,100,324 A | 7/1978 | Anderson et al. |
| 4,191,609 A | 3/1980 | Trokhan |
| 4,208,459 A | 6/1980 | Becker et al. |
| 4,295,976 A | 10/1981 | Dessaint et al. |
| 4,340,563 A | 7/1982 | Appel et al. |
| 4,488,928 A | 12/1984 | Ali Khan et al. |
| 4,637,859 A | 1/1987 | Trokhan |
| 4,798,603 A | 1/1989 | Meyer et al. |
| 5,068,225 A | 11/1991 | Pennell et al. |
| 5,134,229 A | 7/1992 | Saferstein et al. |
| 5,176,668 A | 1/1993 | Bernardin |
| 5,176,672 A | 1/1993 | Bruemmer et al. |
| 5,192,606 A | 3/1993 | Proxmire et al. |
| 5,216,057 A | 6/1993 | Pratt et al. |
| 5,284,703 A | 2/1994 | Everhart et al. |
| 5,350,067 A | 9/1994 | Beltran |
| 5,350,624 A | 9/1994 | Georger et al. |
| 5,505,943 A | 4/1996 | Fortney et al. |
| 5,509,915 A | 4/1996 | Hanson et al. |
| 5,597,567 A | 1/1997 | Whitcup et al. |
| 5,641,783 A | 6/1997 | Klein et al. |
| 5,646,178 A | 7/1997 | Walker et al. |
| 5,679,658 A | 10/1997 | Elson |
| 5,716,625 A | 2/1998 | Hahn et al. |
| 5,756,107 A | 5/1998 | Hahn et al. |
| 5,785,993 A | 7/1998 | Baker et al. |
| 5,791,352 A | 8/1998 | Reich et al. |
| 5,804,203 A | 9/1998 | Hahn et al. |
| 5,863,663 A | 1/1999 | Mackey et al. |
| 5,885,599 A | 3/1999 | Peterson et al. |
| 6,004,584 A | 12/1999 | Peterson et al. |

(Continued)

FOREIGN PATENT DOCUMENTS

EP 0 561 489 A2 9/1993

(Continued)

OTHER PUBLICATIONS

Aniansson, Gustav et al., "Anti-Adhesive Activity of Human Casein Against *Streptococcus pneumoniae* and *Haemophilus influenzae*," *Microbial Pathogenesis: Molecular and Cellular Biology of Infectious Disease*, vol. 8, No. 5, May 1990, pp. 315-323.

(Continued)

*Primary Examiner*—Jacqueline F. Stephens
(74) *Attorney, Agent, or Firm*—H. Michael Kubicki

(57) ABSTRACT

The present invention provides a topical composition for application to the perianal and/or labial areas of the skin which helps prevent viscoelastic fluids, such as menses and feces, from attaching to the skin and aids in the reducing the viscoelastic properties of the fluid so that the fluid can flow into absorbent articles. The composition contains at least one viscoelastant material and at least one an anti-adherent material. the composition may be applied with a wipe, including mitts and gloves, a solid stick composition, an aerosol dispenser, a pump spray, a trigger spray, a squeeze bottle, as a foam, as a cream, as an ointment, as a salve, as a gel, as a wash or as a lotion. In addition, absorbent articles, such as pads or pants, diapers and the like may also be used as a means to transfer the composition to the skin.

10 Claims, No Drawings

U.S. PATENT DOCUMENTS

| | | | |
|---|---|---|---|
| 6,013,679 | A | 1/2000 | Kuo et al. |
| 6,030,995 | A | 2/2000 | Shayman et al. |
| 6,060,636 | A | 5/2000 | Yahiaoui et al. |
| 6,118,041 | A | 9/2000 | Roe et al. |
| 6,133,325 | A | 10/2000 | Schwartz et al. |
| 6,139,850 | A | 10/2000 | Hahn et al. |
| 6,178,922 | B1 | 1/2001 | Denesuk et al. |
| 6,271,331 | B1 | 8/2001 | Gay et al. |
| 6,287,581 | B1 | 9/2001 | Krzysik et al. |
| 6,303,125 | B1 | 10/2001 | Ofek et al. |
| 6,340,664 | B1 | 1/2002 | Gassenmeier et al. |
| 6,359,097 | B1 | 3/2002 | Jost et al. |
| 6,407,141 | B1 | 6/2002 | Hart |
| 6,436,481 | B1 | 8/2002 | Chabrecek et al. |
| 6,440,471 | B2 | 8/2002 | Walker et al. |
| 6,486,140 | B2 | 11/2002 | Hansson et al. |
| 6,500,539 | B1 | 12/2002 | Chen et al. |
| 6,503,526 | B1 | 1/2003 | Krzysik et al. |
| 6,538,097 | B2 | 3/2003 | Yamaguchi et al. |
| 6,558,941 | B2 | 5/2003 | Zuelli et al. |
| 6,623,761 | B2 | 9/2003 | Hassan |
| 6,756,520 | B1 * | 6/2004 | Krzysik et al. ............... 604/360 |
| 2002/0058056 | A1 | 5/2002 | Yahiaoui et al. |
| 2004/0064117 | A1 | 4/2004 | Hammons et al. |
| 2004/0191279 | A1 | 9/2004 | Klofta |
| 2004/0193126 | A1 | 9/2004 | Roe et al. |
| 2006/0140899 | A1 | 6/2006 | Koenig et al. |

FOREIGN PATENT DOCUMENTS

| | | |
|---|---|---|
| EP | 0 443 043 B1 | 4/1995 |
| EP | 0 626 843 B1 | 10/1997 |
| EP | 0 792 322 B1 | 5/1999 |
| EP | 0 792 323 B1 | 6/1999 |
| EP | 0 992 518 A1 | 4/2000 |
| EP | 0 732 110 B1 | 10/2001 |
| EP | 1 152 013 A1 | 11/2001 |
| EP | 0 642 351 B1 | 3/2002 |
| EP | 0 831 856 B1 | 8/2002 |
| EP | 1 238 949 A1 | 9/2002 |
| EP | 1 241 227 A1 | 9/2002 |
| EP | 0 772 446 B1 | 10/2002 |
| EP | 1 245 247 A1 | 10/2002 |
| EP | 1 262 200 A2 | 12/2002 |
| JP | 2832517 B2 | 10/1998 |
| JP | 2002-128892 | 5/2002 |
| WO | WO 94/14472 A1 | 7/1994 |
| WO | WO 95/26197 A1 | 10/1995 |
| WO | WO 95/33467 A2 | 12/1995 |
| WO | WO 96/04003 A1 | 2/1996 |
| WO | WO 96/19182 A1 | 6/1996 |
| WO | WO 96/24371 A1 | 8/1996 |
| WO | WO 96/37519 A1 | 11/1996 |
| WO | WO 97/17085 A2 | 5/1997 |
| WO | WO 97/18790 A2 | 5/1997 |
| WO | WP 98/16104 A1 | 4/1998 |
| WO | WO 98/47546 A1 | 10/1998 |
| WO | WO 98/53800 A1 | 12/1998 |
| WO | WO 99/12541 A1 | 3/1999 |
| WO | WO 99/26610 A1 | 6/1999 |
| WO | WO 00/00226 A1 | 1/2000 |
| WO | WO 00/10500 A1 | 3/2000 |
| WO | WO 00/17371 A1 | 3/2000 |
| WO | WO 00/71139 A2 | 11/2000 |
| WO | WO 01/00156 A1 | 1/2001 |
| WO | WO 01/05370 A1 | 1/2001 |
| WO | WO 01/06973 A1 | 2/2001 |
| WO | WO 01/72262 A2 | 10/2001 |
| WO | WO 01/91684 A2 | 12/2001 |
| WO | WO 02/05839 A1 | 1/2002 |
| WO | WO 02/07746 A1 | 1/2002 |
| WO | WO 02/09792 A1 | 2/2002 |
| WO | WO 02/080668 A2 | 10/2002 |
| WO | WO 02/085315 A2 | 10/2002 |
| WO | WO 02/094864 A2 | 11/2002 |
| WO | WO 03/004070 A1 | 1/2003 |
| WO | WO 03/005982 A1 | 1/2003 |
| WO | WO 03/051327 A1 | 6/2003 |
| WO | WO 2004/004679 A1 | 1/2004 |
| WO | WO 2004/004793 A1 | 1/2004 |
| WO | WO 2006/022960 A1 | 3/2006 |
| WO | WO 2006/022961 A1 | 3/2006 |

OTHER PUBLICATIONS

Asakura, Shinji et al., "Inhibition of Cell Adhesion by High Molecular Weight Kininogen," *The Journal of Cell. Biology*, vol. 116, No. 2, Jan. 1992, pp. 465-476.

Barghouthi, Sameer et al., "Inhibition by Dextran of *Pseudomonas aeruginosa* Adherence to Epithelial Cells," *American Journal of Respiratory and Critical Care Medicine*, vol. 154, No. 4, Oct. 1996, pp. 1788-1793.

Calderone, Richard A. and Phyllis C. Braun, "Adherence and Receptor Relationships of *Candida albicans*," *Microbiological Reviews*, vol. 55, No. 1, Mar. 1991, pp. 1-20.

Chiguet-Ehrismann, Ruth "Anti-Adhesive Molecules of the Extracellular Matrix," *Current Opinion in Cell Biology*, vol. 3, No. 5, Oct. 1991, pp. 800-804.

Chiu, Cheng-Hsun et al., "Adherence of *Burkholderia cepacia* to Respiratory Tract Epithelial Cells and Inhibition with Dextrans," *Microbiology*, vol. 147, Pt. 10, Oct. 2001, pp. 2651-2658.

Chrétien, F.C. and M. Guignard, "Improvement of Human Ovulatory Cervical Mucus by Alpha-Amylase. Effect on Spinability and Crystallization In Vitro," *European Journal of Clinical Pharmacology*, vol. 35, No. 4, 1988, pp. 345-352.

Feng, Wei et al., "Improved Clearability of Cystic Fibrosis Sputum with Dextran Treatment in Vitro," *American Journal of Respiratory and Critical Care Medicine*, vol. 157, No. 3, Pt. 1, Mar. 1998, pp. 710-714.

Guzman-Murillo, M.A. and F. Ascencio, "Anti-Adhesive Activity of Sulphated Exopolysaccharides of Microalgae on Attachment of Red Sore Disease-Associated Bacteria and *Helicobacter pylori* to Tissue Culture Cells," *The Society for Applied Microbiology: Letters in Applied Microbiology*, vol. 30, No. 6, Jun. 2000, pp. 473-478.

Hostetter, Margaret K. "Adhesins and Ligands Involved in the Interaction of *Candida* Spp. with Epithelial and Endothelial Surfaces," *Clinical Microbiology Reviews*, vol. 7, No. 1, Jan. 1994, pp. 29-42.

Kelly, Charles G. and Justine S. Younson, "Anti-Adhesive Strategies in the Prevention of Infectious Disease at Mucosal Surfaces," *Expert Opinion on Investigational Drugs*, vol. 9, No. 8, Ashley Publications Ltd., Aug. 2000, pp. 1711-1721.

Kemp, B. et al., "Does Vascular Endothelial Growth Factor (VEGF) Play a Role in Cyclic Changes of the Cervix?" *Geburtshilfe und Frauenheilkunde*, vol. 61, No. 9, Sep. 2001, pp. 671-675.

Khaled, Zahangir et al., "Multiple Mechanisms May Contribute to the Cellular Anti-Adhesive Effects of Phosphorothioate Oligodeoxynucleotides," *Nucleic Acids Research*, vol. 24, No. 4, Feb. 15, 1996, pp. 737-745.

Kozai, Katsuyuki et al., In Vitro Study of Antibacterial and Antiadhesive Activities of Fluoride-Containing Light-Cured Fissure Sealants and a Glass Ionomer Liner/Base Against Oral Bacteria, *Journal of Dentistry for Children*, vol. 67, No. 2, Mar.-Apr. 2000, pp. 117-122.

Lilly Research Laboratories, "Biochemical Properties and Cellular Effects of Prostate Specific Antigen," *Proceedings of the Annual Meeting of the American Association of Cancer Research*, vol. 38, 1997, (ISSN 0197-016X), 1 page.

Lundmark, Karin et al., "Perlecan Inhibits Smooth Muscle Cell Adhesion to Fibronectin: Role of Heparan Sulfate," *Journal of Cellular Physiology*, vol. 188, No. 1, Jul. 2001, pp. 67-74.

Mannucci, P.M. et al., "Beta-Benzal-Butyric Acid, A New Anti-Adhesive Drug," *Acta Univ. Carol Med. Monogr.*, vol. 53, 1972, pp. 409-412.

Melani, D. et al., "A Review of Human Cervical Mucus Enzymes," *Sci/PerBio—European Journal of Fertility and Sterility*, Acta Europaea Fertilitatis, Special Contribution, vol. 22, No. 6, Nov.-Dec. 1991, pp. 305-313.

Morra, Marco and Clara Cassineli, Non-Fouling Properties of Polysaccharide-Coated Surfaces, *Journal of Biomaterials Science: Polymer Edition*, vol. 10, No. 10, 1999, pp. 1107-1124.

Mortell, Heather, "Proteolysis of Cervical Mucus for Improved Performance in Absorbent Products," published electronically as document No. 32016D at Internet web site "www.ip.com" on Oct. 19, 2004, 3 pages.

Pavesio, Alessandra et al., "Anti-Adhesive Surfaces Through Hyaluronan Coatings," *Medical Device Technology*, vol. 8, No. 7, Sep. 1997, pp. 20-21, 24-27.

Portolés, Marta et al., "Poloxamer 407 as a Bacterial Abhesive for Hydrogel Contact Lenses," *Journal of Biomedical Materials Research*, vol. 28, No. 3, Mar. 1994, pp. 303-309.

Robbins, R.C., "Flavones in Citrus Exhibit Antiadhesive Action on Platelets," *International Journal for Vitamin and Nutrition Research*, vol. 58, No. 4, 1988, pp. 418-421.

Roberfroid, M., "Dietary Fiber, Inulin, and Oligofructose: A Review Comparing Their Physiological Effects," *Critical Reviews in Food Science and Nutrition*, vol. 33, No. 2, 1993, pp. 103-148.

Rocha, H.A. O. et al., "A Fucan from the Brown Seaweed *Spatoglossum Schröederi* Inhibits Chinese Hamster Ovary Cell Adhesion to Several Extracellular Matrix Proteins," *Brazillian Journal of Medical and Biological Research*, vol. 34, No. 5, May 2001, pp. 621-626.

Schier, F. et al., "Hyaluronate, Tetrachlorodecaoxide, and Galactolipid Prevent Adhesions After Implantation of Gore-Tex and Dura Mater into the Abdominal Wall in Rats," *Pediatr. Surg. Int.*, vol. 15, Nos. 3-4, 1999, pp. 255-259.

Sharon, Nathan, "Safe as Mother's Milk: Carbohydrates as Future Anti-Adhesion Drugs for Bacterial Diseases," Glycoconiugate Journal, vol. 17, Nos. 7-9, Jul.-Sep. 2000, pp. 659-664.

Tronchin, G. et al., "Fungal Cell Adhesion Molecules in *Candida albicans*," *European Journal of Epidemiology*, vol. 7, No. 1, Jan. 1991, pp. 23-33.

Yin, H.-Z. et al., "Gelatinolytic Proteinase Activities in Human Seminal Plasma," *Journal of Reproduction & Fertility*, vol. 88, 1990, pp. 491-501.

* cited by examiner

COMPOSITION AND WIPE FOR REDUCING VISCOSITY OF VISCOELASTIC BODILY FLUIDS

FIELD OF THE INVENTION

The present invention relates to a composition and a wipe containing the composition which reduces the viscosity of viscoelastic bodily fluids, such as menses and feces. More particularly, the present invention relates to a composition which contains a viscoelastant and an anti-adherent. The present invention also relates to a wipe containing the viscoelastant and optionally an anti-adherent that this used to apply the viscoelastant and optional anti-adherent to the labial and/or perianal areas of the body.

BACKGROUND OF THE INVENTION

Menses is a viscoelastic fluid composed of blood (primarily red blood cells and plasma), cervical mucus and/or tissue fragments. Mucin is found in virtually all menses samples. Mucin is a large linear glycoprotein having molecular weights up to 20 million or more. In combination with water and salts, mucin is a principal component of mucus, including cervical mucus. Mucin, with its large linear molecules, is believed to form networks in solution, giving rise to the viscoelastic properties of menses.

As menses and other non-menstrual fluids exit the vagina, they often wick along the body, causing the fluids to remain on the skin or on hair located in this region, causing the fluid to dry out and remain on the skin and/or hair. When absorbent articles are used to absorb and contain these fluids, often the fluids do not reach the absorbent article so that the absorbent article will be able to absorb and contain the desired fluids. The failure of the fluids to reach the absorbent article is often due to the viscoelastic properties of menses and menses preferred attraction to the skin. As a result of these fluids remaining on the skin, a number of undesirable situations may occur, including, transfer of the fluids to undergarments, staining of undergarments and unwanted odors.

Absorbent materials and absorbent articles are known in the art and are known to have a wide variety of uses, in particular for absorbing bodily fluids. Examples of such absorbent materials and absorbent articles include, for example; personal care products, such as disposable diapers and training pants; feminine hygiene products, such as sanitary napkins and tampons; incontinent care products, such as pads and undergarments and the like. As is mentioned above, some fluids designed to be absorbed by these articles sometimes do not reach the absorbent article, due to the fluids being deposited on skin and hair. In addition, highly viscous fluids are often difficult to absorb into absorbent articles. For example, in feminine hygiene products, the viscoelastic properties of menses often make it challenging to absorb and distribute within the feminine hygiene products. The viscosity and/or elastic components of such fluids tend to impose requirements for absorption and/or distribution within the absorbent structure of the absorbent product.

In addition, mucin causes many challenges in menses absorbent articles. Mucin in menses reduces intake of the menses fluid through the cover or body facing surface of an absorbent article. In addition, mucin tends to hamper fluid distribution in the absorbent article due to its highly viscoelastic and stringy nature. It is believed that mucin forms a three-dimensional network on the surface of the absorbent article, thereby blocking the intake ability of the absorbent article. When additional insults of menses come into contact with the three-dimensional network on the surface of the absorbent article, the additional insults may flow over the three-dimensional network, thereby causing the absorbent article to leak. Further, if the mucin component does penetrate the surface of the absorbent article, the mucin may clog the pores of the underlying absorbent layers, thereby causing a local saturation (most, if not all, of the pores in an area being filled to capacity) of the absorbent layer and/or the intake layer. The local saturation may cause leakage, especially with subsequent insults or prevent further distribution of the menses in the x, y and z directions within the absorbent article or individual layers which may be present in an absorbent article, leading to leakage or fluid remaining on the pad surface, which in turn leads to skin wetness.

Over the course of many years, a number of commercially available products have been developed to assist individuals in cleaning themselves in the labial and perianal regions of the body. Conventional bath tissues have been used for many years and, recently, flushable wet bath tissues have been introduced. These products may be used alone, or in combination, to effectuate cleansing of the perianal and labial regions.

Proper cleaning skin in the perianal and vaginal regions can be difficult due to the topography of the skin in that region and the presence of hair follicles. A common problem encountered by many individuals during cleaning of these areas after bowel movements or during menstruation is the occasional sticking of fecal material or the frequent occurrence of menses to the skin in the perianal and labial areas. Additionally, because fecal material generally contains bacteria and active enzymes, the presence of this material in the perianal region after bowel movement cleanup can also result in skin irritation, redness, and even inflammation and infection for sensitive individuals. Residual menstrual fluid can support the accumulation of organic material which can persist with subsequent cleanings. These residues contain bacteria, yeast, enzymes, odor inducing agents, and microbial growth promoters. These factors can alone or in combination cause skin irritation, itching sensations, infections, as well as personal discomfort.

Based on the foregoing, it is clear that maintaining clean and healthy skin in the perianal, labial and surrounding areas is difficult, yet important. As such, products that can improve cleaning of the skin in these regions are highly desirable, as are products which can aid in transferring the viscoelastic fluids from the body to the absorbent articles to maintain clean skin in between product changes. It would also be desirable for the products to be flushable and of low cost.

SUMMARY OF THE INVENTION

Generally stated, the present invention provides a topical composition for the application to the perianal and/or labial areas of the skin which helps prevent viscoelastic fluids, such as menses and feces, from attaching to the skin and/or aids in reducing the viscoelastic properties of the fluid so that the fluid can flow directly to and into absorbent articles. The composition contains at least one viscoelastant material and optionally at least one an anti-adherent material.

In another aspect of the present invention the composition contains between about 0.01% to about 25% by weight of the viscoelastant material and optionally between about 0.01% to about 25% by weight of an anti-adherent material. Exemplary viscoelastant materials include linked enzymes, alkyl polyglycosides having 8-10 carbon atoms in the alkyl chain, bovine lipid extract surfactant, dextrans and dextran derivatives. Exemplary anti-adherent materials include alginic acid, beta-benzal-butyric acid, botanicals, casein, farnesol, flavones, fucans, galactolipid, kininogen, hyaluronate, inulin, iridoid glycosides, nanoparticles, perlecan, phosphorothioate oligodeoxynucleotides, poloxamer 407, polymethylmethacrylate, silicone, other silicone containing compositions, sulphated exopolysaccharides, tetrachlorodecaoxide, and combinations thereof.

In another aspect of the present invention other components may be added to the composition, including a skin conditioning agent, a structuring agent and a rheology modifier which may aid in transferring the composition to the body. Typically, the skin conditioning agent is present in an amount from about 20% to about 90% by weight of the total composition; the structuring agent, when present, is present in an amount from about 10% to about 70% by weight of the total composition; and the rheology modifier, when present, is present in an amount from about 1% to about 25% by weight of the total composition.

In another aspect of the present invention, the composition may be applied with a wipe, including mitts and gloves, a solid stick composition, an aerosol dispenser, a pump spray, a trigger spray, as a wash as a foam, as a cream, as an ointment, as a salve, as a gel or as a lotion.

DEFINITIONS

It should be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

As used herein, the term "viscoelastic" means a composition having at least one significant component that is moderately viscous and/or has elastic properties. By "moderately viscous" it is meant that the component has a viscosity of at least that of normal human blood plasma. By "elastic" it is meant that the component has elasticity equal to or greater than normal human blood.

As used herein, the term "viscoelastant" means an organic agent that, when an effective amount is contacted by a viscoelastic composition, materially alters the properties of that viscoelastic composition, for example, by reducing its viscosity and/or elastic nature. By "materially alters" it is meant that the property measured is changed by at least a statistically significant amount and, advantageously, this change will be at least about 30% for many applications.

As used herein, the term "linked enzyme" means an enzyme which is chemically bonded by covalent or ionic bonding to a carrier material which is soluble or dispersible in a solution. This term is also intended to cover a mixture of two or more enzymes chemically bonded to a carrier material.

As used herein, the term "semisolid" means that the composition has a rheology typical of pseudoplastic or plastic liquids. When no shear is applied, the compositions can have the appearance of a semi-solid but can be made to flow as the shear rate is increased. Without intending to be bound by theory, it is believed that while such compositions contain primarily solid components, they also include some liquid components As used herein, the term "nonwoven fabric or web" means a web having a structure of individual fibers or threads which are interlaid, but not in a regular or identifiable manner as in a knitted fabric. The term also includes individual filaments and strands, yarns or tows as well as foams and films that have been fibrillated, apertured, or otherwise treated to impart fabric-like properties. Nonwoven fabrics or webs have been formed from many processes such as for example, meltblowing processes, spunbonding processes, airlaying processes and bonded carded web processes. The basis weight of nonwoven fabrics is usually expressed in ounces of material per square yard (osy) or grams per square meter (gsm) and the fiber diameters useful are usually expressed in microns. (Note that to convert from osy to gsm, multiply osy by 33.91).

As used herein, the term "spunbonded fibers" refers to small diameter fibers which are formed by extruding molten thermoplastic material as filaments from a plurality of fine, usually circular capillaries of a spinneret with the diameter of the extruded filaments then being rapidly reduced as, for example, described in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartmann, and U.S. Pat. No. 3,542,615 to Dobo et al. Spunbond fibers are quenched and generally not tacky when they are deposited onto a collecting surface. Spunbond fibers are generally continuous and have average diameters frequently larger than 7 microns, more particularly, between about 10 and 20 microns.

As used herein, the term "meltblown fibers" means fibers formed by extruding a molten thermoplastic material through a plurality of fine, usually circular, die capillaries as molten threads or filaments into converging high velocity, usually heated, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface often while still tacky to form a web of randomly dispersed meltblown fibers. Such a process is disclosed, for example, in U.S. Pat. No. 3,849,241 to Butin. Meltblown fibers are microfibers which may be continuous or discontinuous and are generally smaller than 10 microns in average diameter.

As used herein, the term "coform material" or "coform" generally refers to composite materials comprising a stabilized matrix of thermoplastic fibers and a second non-thermoplastic material. As an example, coform materials may be made by a process in which at least one meltblown die head is arranged near a chute through which pulp and/or other absorbent materials are added to the web while it is forming. Suitable absorbents include, but are not limited to, fibrous organic materials such as woody or non-woody pulp such as cotton, rayon, recycled paper, wood pulp fluff, cellulose and/or cellulosic staple fibers, and also include inorganic absorbent materials such as superabsorbent materials and/or treated polymeric staple fibers. Exemplary coform materials are disclosed in commonly assigned U.S. Pat. No. 5,284,703 to Everhart et al., U.S. Patent No. 5,350,624 to Georger et al., and U.S. Pat. No. 4,100,324 to Anderson et al.; the entire contents of each of the aforesaid references are incorporated herein by reference.

As used herein, "bonded carded webs" or "BCW" refers to nonwoven webs formed by carding processes as are known to those skilled in the art and further described, for example, in coassigned U.S. Pat. No. 4,488,928 to Alikhan and Schmidt which is incorporated herein in its entirety by reference. Briefly, carding processes involve starting with a blend of, for example, staple fibers with bonding fibers or other bonding components in a bulky batt that is combed or otherwise treated to provide a generally uniform basis weight. This web is heated or otherwise treated to activate the adhesive component resulting in an integrated, usually lofty nonwoven material.

"Airlaying" or "airlaid web" is a well known process by which a fibrous nonwoven layer can be formed. In the airlaying process, bundles of small fibers are separated and entrained in an air supply and then deposited onto a forming screen, usually with the assistance of a vacuum supply. The randomly deposited fibers then are bonded to one another using, for example, hot air or a spray adhesive.

As used herein, the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configuration of the material. These configurations include, but are not limited to isotactic, syndiotactic and random symmetries.

It should be understood that the term "personal care article" as used herein refers to any article used to control bodily fluids, and includes "absorbent products," which refers to any article configured to absorb and retain bodily exudates, including urine, bowel movements, blood and menses, and includes such a product in a packaged and unpackaged configuration. As such, personal care products, as used herein, includes without limitation, diapers, child toilet training pants, adult incontinence garments, male incontinence products, tampons, vaginal suppositories, panty liners, pads, sanitary napkins, tissues, wipes, etc. Examples of commercially available personal care products include, without limitation, Poise® adult care products, including pantiliners and pads, and Kotex® feminine care products, including pads, tampons and liners, Depend® undergarments, underwear and guards, all available from Kimberly-Clark Corporation, Neenah, Wis.

DETAILED DESCRIPTION OF THE INVENTION

The present invention provides a topical viscoelastic fluid modifying composition for the topical application to skin in the perianal and/or labial areas of skin comprising at least one viscoelastant material and optionally at least one anti-adherent material.

The viscoelastant usable in the present invention can be any material which will reduce the viscoelastic nature of viscoelastic fluids. Examples of suitable viscoelastant materials include viscoelastant agents such as alkyl polyglycosides having 8-10 carbon atoms in the alkyl chain, which are described in U.S. Pat. No. 6,060,636 to Yahiaoui et al. Other examples of viscoelastants include bovine lipid extract surfactant (Survanta, Ross Laboratories), a drug used to treat Acute Respiratory Distress Syndrome and Cystic Fibrosis. Some dextrans and dextran derivative, such as dextran sulfate, may also be used as viscoelastants. Dextrans are polymers of glucose with chain-like structures and molecular weights up to, for example, 2,000,000 daltons produced from sucrose, often by bacterial action. An exemplary dextran is a 4000 MW dextran available from Polydex Pharmaceuticals, Ltd. Of Scarborough, Canada. Linked enzymes may also be used.

The enzyme can be any type of enzyme. Exemplary enzymes include amylase, lysozyme, zymolyase, celulase, protease, lipase, urease, elastase, carbohydrase, cathepsin G, myeloperoxidase, cytolysins, such as phospholipase and listeriolysin, streptolysin, perfringolysin, and combinations thereof. The enzyme is selected based on its ability to modify the viscosity the components present in viscoelastic material to be absorbed into the treated substrate. For example, if the viscoelastic material is a protein based fluid, the enzyme could be a protease. Likewise, if the viscoelastic fluids are carbohydrates, the enzyme could be a glycosidase. In the present invention, it is desirable that the enzyme is a protease since most viscoelastic bodily fluids contain proteins. Suitably, the protease is papain, bromelain, pepsin, trypsin, chymotrypsin, serine proteases or mixtures thereof. Exemplary glycosidases include, for example, an α-amylase, neuraminidase, α- or β-glucosidase, galactosidase, glycosynltransferases and the like. Also mixtures of glycosidases and proteases may be used when the viscoelastic fluid has both protein and carbohydrate, or either the protease or glycosidase may be used. For example, if the viscoelastic fluid is a fluid such as mucus, which is mucin and water, the enzyme could be a protease, a glycosidase or mixtures thereof.

The enzyme may be linked to a carrier material. Generally, it is desirable that the enzyme is linked or chemically bonded by covalent or ionic bonding to a carrier material. Ideally, the carrier material is a material which is soluble or dispersible in a solution, in particular, aqueous solutions. The carrier material can be a polymer, or a compound which is dispersible or soluble in solutions. In addition, the carrier can be a material which can be formed into micelles. More desirably, the polymer is soluble or dispersible in an aqueous solution. Desirable the carrier substrate is soluble in a liquid, more desirably the carrier material should be soluble in water. Polymers useable in the present invention as the carrier material include, for example, polyacrylic acid, polyvinylpyrrolidone, polyalkylene oxide, such as polyethylene glycol, polyvinyl alcohol, maleic anhydride polymers and copolymers such as acrylamide-maleic acid hydrogels or ethylene maleic anhydride copolymer and block, graft or random copolymers thereof. Other soluble polymers may also be used. One or more enzymes may be linked to a given carrier material or one or more carrier materials may be used for a given enzyme. For example, the carrier may be a polymer mixture. In addition, the linked enzyme may be a blend of two or more linked enzymes, each having the same or different carrier materials.

Linking of the enzyme can be carried out by techniques known to those skilled in the art. Such techniques are described in U.S. Pat. No. 3,625,827 to Wildi et al. and U.S. Pat. No. 3,616,229 to Wildi et al., both of which are hereby incorporated by reference in their entirety. Generally described, the enzyme or mixture of enzymes are reacted with a polymer in a solution. Desirably, the enzyme is reacted through a group on the enzyme which does not affect the activity of the enzyme once linked to the carrier material. Exemplary reactive groups which generally do not affect the enzymatic activity usually present on enzymes include, for example, amino, hydroxyl, carboxyl, anhydride, mercapto and imidazolyl groups. These groups can be reacted with polymers that are adapted to react or couple with the enzyme (s). Effective reactive groups on the polymers include, for example, carboxyl groups, anhydride groups, amino groups, hydroxyl groups, mercapto groups and the like. The reaction can result in bonding between the enzyme(s) and the polymer which may be ionic or covalent bonding. In some situations, which will be apparent to those skilled in the art, it may be necessary to protect the active groups of the enzyme which give the enzyme its activity from reaction with the reactive groups of the polymer. In such cases, the protecting group must be readily removable from the enzyme and such protecting techniques are readily apparent to those skilled in the art. Other possible methods of linking enzymes to carriers could include reacting the carrier with one functional group of a polyfunctional compound, followed by reacting another functional group of the polyfunctional compound with the enzyme.

One exemplary enzyme is papain, an enzyme obtained from unripe papaya. Papain linked to a polymer carrier is commercially available under the tradename Linked-Papain®). Linked-Papain® (papain carbomer, as described in CTFA, the International Cosmetic Ingredients Dictionary) is the enzyme papain in which papain is covalently linked to polyacrylic acid (900,000 daltons). Linked-Papain® is commercially available from Collaborative Laboratories, 3 Technology Drive, East Setauket, N.Y. 11733).

If a linked enzyme is used, care should be taken so that the linked enzyme does not cause irritation to the sensitive skin in the labial and perianal regions of the body.

Other possible viscoelasants may include components of seminal fluid. The full and complete mechanisms responsible for autonomous liquefaction of cervical mucus at ovulation or upon fertilization have not, to our knowledge, been conclusively determined. Candidates for roles in liquefaction of cervical mucus include numerous enzymes in cervical mucus or seminal fluid. These include vascular endothelial growth factor 165 and amylases, which are present in cervical mucus, and prostate specific antigen, present in semen. The proteolytic activities of various other enzymes in semen and cervical mucus have been noted, but the specific enzymes responsible for these activities have not, as near as we have been able to determine, been identified. For selected references in this area, see Melani, D.; Ranaldi, F.; Giachetti, E.; Vanni, P. *Acta Eur. Fertil.* 1991, 22, 305-313; Yin, H.-Z.; Vogel, M. M.; Schneider, M.; Ercole, C.; Zhang, G.; Sinha, A. A.; Wilson, M. J. *J. Reprod. Fert.* 1990, 88, 491-501; Kemp, B.; Classen-Linke, I.; Schlehe, B.; Beier, H. M.; Rath, W. *Geburtshilfe Frauenheilkd.* 2001, 61, 671-675; Chrétien, F. C.; Guignard, M. *Eur. J. Clin. Pharmacol.* 1988, 35, 345-352; and meeting abstract: Biochemical Properties and Cellular Effects of Prostate Specific Antigen; *Proc. Annu. Meet. Am. Assoc. Cancer Res.* 1997, 38., Each of these are incorporated by reference.

The anti-adherent compound included in the topical composition described herein acts to prevent the adherence of menses and/or fecal material to the skin in the labial and perianal regions during and after menstruation or defecation, respectively. The presence of the anti-adherent compound in the formulation results in a decreased amount of menstrual and/or fecal material in the labial and/or anal region during menstruation or after a bowel movement. Without being bound to a particular theory, it is believed that the anti-adherent compound attaches to the skin through electrical and hydrophobic interaction with the skin and remains tightly bound thereto after deposit. When defecation occurs, bacteria and enzymes in the fecal material, which also typically attach to skin through electrical interactions, are not able to make the attachment to the skin as many of the binding sites are already occupied with anti-adherent compound. Because electrical and hydrophilic interaction with the bacteria and enzymes and the skin is reduced, much less fecal matter remains attached to the skin after defecation.

Suitable anti-adherent compounds include alginic acid, beta-benzal-butyric acid, botanicals, casein, farnesol, flavones, fucans, galactolipid, kininogen, hyaluronate, inulin, iridoid glycosides, nanoparticles, perlecan, phosphorothioate oligodeoxynucleotides, poloxamer 407, polymethylmethacrylate, silicone, sulphated exopolysaccharides, tetrachlorodecaoxide, and combinations thereof.

The topical composition of the present invention typically contains from about 0.01% to about 25% by weight of the viscoelastant material and optionally between about 0.01% to about 25% by weight of an anti-adherent material. More typically, the composition contains from about 0.05% to about 10% by weight of the viscoelastant material and between about 0.05% to about 10% by weight of an anti-adherent material, and most typically from about 0.1% to about 8% by weight of the viscoelastant material and between about 0.1% to about 5% by weight of an anti-adherent material.

Depending on the nature of the materials selected for the composition, some materials may function both as a viscoelastant and an anti-adherent.

Other ingredients may also be added to the composition of the present invention to promote adhesion of the composition to the skin or aid in the transfer of the composition to the skin. The other ingredients include, for example, a skin conditioning agent, a structuring agent and a rheology modifier.

A skin conditioning agent emollient is an active ingredient in the topical composition of the present invention that typically softens, soothes, supples, coats, lubricates, cleans and/or moisturizes the skin. There are three types of skin conditioning agents. One type of skin conditioning agent, generally referred to as emollients, are particularly useful in improving the dry skin condition by restoring its moisture level as well as its softness, smoothness, pliability, and flexibility. A second type of skin conditioning agents, generally referred to as moisturizers or humectants, attract moisture from the surrounding atmosphere and enhance the water absorption of the stratum corneum (i.e., the outer, corny layer of the skin). A third type of skin conditioning agents, generally referred to as barrier protestants, which form an occlusive (i.e., non-water-permeable) layer on the skin surface that prevents or retards moisture losses from the deeper layers of the skin to the atmosphere. Exemplary skin conditioning agents useful in the present invention include, but are not limited to the following classes of compounds: petroleum-based emollients; fatty acid esters; polysiloxanes; polyol polyesters; esters or ethers of polyhydroxy alcohols; fatty alcohol esters of polyprotonic acids; animal oils, fats, and their derivatives; vegetable oils, hydrogenated vegetable oils, and their derivatives; branched hydrocarbons; fatty alcohol ethers; free sterols, sterol esters and their derivatives; phospholipids; and mixtures thereof. These types of compounds are well known in the art.

In one embodiment of the present invention, emollient type of skin conditioning agent are desired. Generally, emollients accomplish several of skin conditioning objectives simultaneously. Typically, emollients suitable for use in the composition described herein are fluids at room temperature such that they impart a soft, lubricious lotion-like feel upon use. Suitable emollients for use in the formulations of the present invention are typically substantially water free. Although the emollient component may contain trace amounts of water as a contaminant without substantially harming the formulation, it is preferred that the amount of water be less than about 5% by weight of the emollient component of the formulation to reduce the likelihood of microbial growth and product destruction.

Suitable emollients for inclusion in the formulations described herein include petrolatum, mineral oil, mineral jelly, isoparaffins, vegetable oils, avocado oil, borage oil, canola oil, castor oil, chamomile, coconut oil, corn oil, cottonseed oil, evening primrose oil, safflower oil, sunflower oil, soybean oil, sweet almond, lanolin, partially hydrogenated vegetable oils, sterols and sterol derivatives, polydimethylsiloxanes, methicone, cyclomethicone, dimethicone, dimethiconol, trimethicone, organo-siloxanes, silicone elastomer, gums, resins, fatty acid esters (esters of $C_6$-$C_{28}$ fatty acids and $C_6$-$C_{28}$ fatty alcohols), glyceryl esters and derivatives, fatty acid ester ethoxylates, alkyl ethoxylates, $C_{12}$-$C_{28}$ fatty alcohols, $C_{12}$-$C_{28}$ fatty acids, $C_{12}$-$C_{28}$ fatty alcohol ethers, Guerbet alcohols, Guerbet Acids, Guerbet Esters, and combinations thereof. Petrolatum and mineral oil are generally desired emollients.

Generally, the skin conditioning agent is present in an amount from about 20% to about 90% by weight of the total composition. More typically, the composition contains from about 30% to about 85% by weight of the skin conditioning agent, and most typically from about 40% to about 80% by weight of the skin conditioning agent.

The structuring agent utilized in the topical composition of the present invention helps to immobilize the skin conditioning agent and other components on the surface of a base substrate of a delivery vehicle, which may be used to deliver the topical composition to the skin. Because some skin conditioning agents, in particular the emollients, are fluids at room temperature, they may tend to flow or migrate away from the surface of the base substrate and into the interior of the base substrate where they are of limited value due to non-transferability, and may tend to decrease the strength of the base substrate due to debonding. The structuring agent reduces the ability of the emollient (and other components) to migrate and keeps the emollient primarily on the surface of the base substrate.

Generally, the structuring agent, when present, is present in an amount from about 10% to about 70% by weight of the total composition. More typically, the composition contains from about 20% to about 65% by weight of the structuring agent, and most typically from about 30% to about 60% by weight of the structuring agent.

Suitable structuring agents include animal waxes, vegetable waxes, mineral waxes, synthetic waxes, polymers, bayberry wax, beeswax, stearyl dimethicone, stearyl trimethicone, $C_{20}$-$C_{22}$ dimethicone, $C_{20}$-$C_{22}$ trimethicone, $C_{24}$-$C_{28}$ dimethicone, $C_{20}$-$C_{22}$ trimethicone, $C_{30}$ alkyl dimethicone, candelilla wax, carnauba, ceresin, cetyl esters, stearyl benzoate, behenyl benzoate, esparto, hydrogenated cottonseed oil, hydrogenated jojoba oil, hydrogenated jojoba wax, hydrogenated microcrystalline wax, hydrogenated rice bran wax, japan wax, jojoba buffer, jojoba esters, jojoba wax, lanolin wax, microcrystalline wax, mink wax, motan acid wax, motan wax, ouricury wax, ozokerite parrafin, PEG-6 beeswax, PEG-8 beeswax, rezowax, rice bran wax, shellac wax, spent grain wax, spermaceti wax, synthetic spermaceti wax, synthetic beeswax, synthetic candelilla wax, synthetic carnuba wax, synthetic japan wax, synthetic jojoba wax, $C_{14}$-$C_{28}$ fatty acid ethoxylates and $C_{14}$-$C_{28}$ fatty ethers, $C_{14}$-$C_{28}$ fatty alcohols, $C_{14}$-$C_{28}$ fatty acids, polyethylene, oxidized polyethylene, ethylene-alpha olefin copolymers, ethylene homopolymers, $C_{18}$-$C_{45}$ olefins, poly alpha olefins, hydrogenated vegetable oils, polyhydroxy fatty acid esters, polyhydroxy fatty acid amides, ethoxylated fatty alcohols and esters of $C_{12}$-$C_{28}$ fatty acids, and esters of $C_{12}$-$C_{28}$ fatty alcohols, and combinations thereof.

The rheology modifier utilized in the topical composition of the present invention increases the melt point viscosity of the formulation so that the formulation readily remains on the surface of the base substrate and does not substantially migrate into the interior of the base substrate, while substantially not affecting the transfer of the anti-adherent formulation to the skin. Additionally, the rheology modifier helps the topical composition to maintain a high viscosity at elevated temperatures, such as those encountered during storage and transportation. Exemplary rheology modifiers include organic materials such as natural or synthetic waxes, $C_{12}$-$C_{60}$ alcohols, $C_{12}$-$C_{60}$ acids, alpha-hydroxy fatty acids, polyhydroxy fatty acid esters, polyhydroxy fatty acid amides, and inorganic/organic materials such as metal ester complexes containing zinc, calcium, aluminum or magnesium, silicas, organoclays and polymeric materials, all of which are known in the art.

Suitable polymeric rheology modifiers include combinations of alpha-olefins and styrene or polyethylene alone or in combination with mineral oil or petrolatum, di-functional alpha-olefins and styrene alone or in combination with mineral oil or petrolatum, combinations of alpha olefins and isobutene, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, distearadimonium hectorite, and stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, styrene-ethylene/propylene copolymers. Of these rheology modifiers, the polymeric and silicas are generally desired from the standpoint of cost and effectiveness.

Generally, the rheology modifier, when present, is present in an amount from about 1% to about 25% by weight of the total composition. More typically, the composition contains from about 2% to about 20% by weight of the rheology modifier, and most typically from about 3% to about 18% by weight of the rheology modifier.

The composition of the present invention may be applied to the target skin area by one of many different delivery vehicles. For example, the composition may be applied with a wipe, including mitts and gloves, a solid stick composition, an aerosol dispenser, a pump spray, a trigger spray, a squeeze bottle, as a foam, as a cream, as an ointment, as a salve, as a gel, as a wash or as a lotion. In addition, absorbent articles, such as pads or pants, diapers and the like may also be used as a means to transfer the composition to the skin. Whichever method is selected, it is desirable that the composition be administered in an acceptable fashion to the target skin area without leaving a messy aesthetically unpleasing residue on the skin. It is further desirable that the composition be administered without direct contact with the users' or applicators' hands, which could result in a messy residue is left on the user's/applicators hands, requiring additional cleaning up after application. Of the methods described above, the application with a wipe has some advantage over the other methods. For example, the wipe may be easily provided in a pouch with a disposable absorbent personal care article.

The composition of the present invention make it is possible to combine in a wipe or other delivery vehicle means such as a spray, foam, lotion cream, ointment, salve, wash, gel or absorbent articles described above, a mixture of anti-adherent compounds and viscoelastic modification compounds which will transfer to the skin. This combination of the viscoelastant and anti-adherent enhances the interaction of both menses and feces with the labial and perianal area skin, such that these fluids will not stick to the skin or hair in these areas, while providing a benefit of improved absorbency to the absorbent article. The improved performance is such that the performance of the absorbent article is greater than it would be with either compound alone. Although not to be bound by theory, it is believed that the enhancement is realized due to the ability of the modifier to reduce the apparent viscosity of the menses or feces such that these fluids will transfer easily through the body side liner of the absorbent article and into the absorbent core for sequestration and subsequent separation from the body. The anti-adherent is a compound which will coat the skin impeding the attachment or association of the soil with the skin. The ability of both the anti-adherent and feces/mucin modification agent to be delivered to the skin by a wipe substrate or other described vehicle above is realized by the use of divergent chemistries. For example, the hydrophobic chemistries of the anti-adherent and hydrophilic chemistries of the viscoelastant allow this composition to function by having the viscoelastant to partition to the top of the anti-adherent film formed on the skin by the anti-adherent. This interaction allows for the direct interaction of the viscoelastic fluid with the viscoelastant agent.

In the present invention, topical skin treating composition may be applied to a delivery vehicle including wipes, films, sponges, cotton balls, tissues, toilet paper and the like. Exemplary wipe materials include, for example, spunbond nonwoven webs, meltblown nonwoven webs, coform nonwoven webs, airlaid nonwoven webs, bonded carded nonwoven webs, hydroentangled nonwoven webs, and laminates of one or more of these types of nonwoven webs, such as a SMS (spunbond-meltblown-spunbond) laminates. In addition, the wipe may contain a film material as a barrier layer to prevent the user or applicator from soiling their hand during application. The wipes may be wet wipes or dry wipes.

In the case of individually wrapped personal care products, such as feminine napkins, tampons and incontinence pads, the interior surface of the wrapper component could be used to deliver the composition of the present invention to the body of the user. Alternatively, the delivery vehicle containing the composition could be placed in the same individually wrapped product separated from the product, wrapped inside the individual product, or wrapped around the individual product. A separate package containing a plurality of delivery vehicles containing the composition of the present invention could be placed within the same package of individually wrapped products or the two packages could be co-packed as a cleaning system.

In the present invention, the composition may be a liquid, a solid or semi-solid at room temperature, depending on the delivery means and other factors. If in the semi-solid or solid state, the composition should desirably soften, plasticize or become flowable at or near skin temperature, or when a slight pressure or shear force is applied to the composition. This will result in the composition readily transferring to the skin.

The composition described above may have specific melt point and process temperature viscosities, as defined herein. These viscosities are important for at least two reasons. First, the higher the melt point or process temperature viscosity, the less likely the composition is to penetrate into the inner surface of the base substrate of a delivery vehicle. The less formulation that is able to penetrate into the interior of the base substrate, results in more formulation on the surface of the base substrate that can transfer to the user's labial and/or anal skin. Secondly, the higher the viscosity of the formulation at or above the melting point of the formulation, the less likely the formulation will be to migrate at typical or adverse storage or temperature conditions.

The topical composition described above have a melt point viscosity of from about 5000 cPs to about 1,000,000 cPs, desirably from about 50,000 cPs to about 800,000 cPs, and more desirably from about 100,000 cPs to about 500,000 cPs. As used herein, the term "melt point viscosity" means the viscosity of the formulation at the point in time when the formulation visually becomes a liquid. Formulations having melt point viscosities in these ranges significantly improve the ability of the formulation to remain on the surface of the base substrate and the formulation maintains a high viscosity at elevated temperatures, such as those encountered during storage and shipment.

Additionally, to improve application to the surface of the base substrate or delivery means, the hydrophobic formulations described herein have a process temperature viscosity of from about 50 cPs to about 50,000 cPs, desirably from about 75 cPs to about 10,000 cPs, and more desirably from about 100 cPs to about 5,000 cPs. The process temperature is typically from about 5° C. to about 10° C. above the melting point of the lotion formulation.

In one embodiment of the present invention, the anti-adherent formulation, or one or more components of the anti-adherent formulation such as the anti-adherent compound, may be encapsulated in a shell material prior to being introduced onto the base substrate. When the pre-wipe is wiped across the labial or perineal region prior to menstruation or the perianal region prior to defecation, the capsules break open due to the shear of the wiping and release the formulation or component(s). Additionally, the wipes may be dispensed from a dispensing unit that, upon dispensing, creates shear and causes the capsules to break and release the formulation or component(s). Suitable microencapsulation shell materials include cellulose-based polymeric materials (e.g., ethyl cellulose), carbohydrate-based materials (e.g., cationic starches and sugars) and materials derived therefrom (e.g., dextrins and cyclodextrins) as well as other materials compatible with human tissues.

The microencapsulation shell thickness may vary depending upon the anti-adherent formulation utilized, and is generally manufactured to allow the encapsulated formulation or component to be covered by a thin layer of encapsulation material, which may be a monolayer or thicker laminate layer, or may be a composite layer. The microencapsulation layer should be thick enough to resist cracking or breaking of the shell during handling or shipping of the product. The microencapsulation layer should also be constructed such that humidity from atmospheric conditions during storage, shipment, or wear will not cause a breakdown of the microencapsulation layer and result in a release formulation or component.

Microencapsulated formulations or components applied directly to the wipes should be of a size such that the user cannot feel the encapsulated shell on the skin during use. Typically, the capsules have a diameter of no more than about 25 micrometers, and desirably no more than about 10 micrometers. At these sizes, there is no "gritty" or "scratchy" feeling on the skin when the wipe is utilized prior to defecation.

The wipes described herein may contain an amount of anti-adherent formulation such that, upon wiping across the labial or perianal region, an effective amount of formulation is transferred to the skin surface and hair located in these regions. Specifically, the wipe may suitably contain from about 1% (by weight of the base substrate) to about 25% (by weight of the base substrate), desirably from about 1% (by weight of the base substrate) to about 10% (by weight of the base substrate). Based on the disclosure herein, one skilled in the art will recognize that various amounts of anti-adherent formulation may be suitable for different end products.

The anti-adherent and viscoelastant formulations described herein can be introduced onto a suitable base substrate or delivery means utilizing various techniques known in the art. For example, the anti-adherent formulation may include a suspending or thickening agent to suspend the formulation such that it can be gravure or flexographically coated, sprayed, ink-jet printed, or slot coated onto the base substrate in the desired amount. Suitable thickening agents may include, for example, clays, cellulose derivatives such as carboxymethyl cellulose and carboxypropyl cellulose, natural gums such as guar gum and xanthan gum, and acrylate polymers.

As will be recognized by one skilled in the art based on the disclosure herein, the wipe products described herein can be manufactured and sold to consumers in various product forms. For example, the wipes could be manufactured and sold in roll form, as individual sheets, or in stacks of individual sheets. In any of these forms, the wipe product can be in wet form similar to a wet wipe, or could be dry to the touch such that a consumer would wet the product prior to use.

In addition to the components of the various topical composition described herein, each formulation may additionally comprise one or more optional components to impart additional benefits to the topical composition of the present invention. Suitable optional components include, for example, skin protectants, anti-oxidants, powders, antibiotics, anti-microbials, anti-inflammatories, fragrances, colorants, vitamin E, aloe extract, preservatives, odor control agents and the like. In the case of sprays and foams, other components, such as solvents, water, emulsifier, foaming agents and the like may be added to the composition so that the composition may be sprayed or foamed as the method of application.

Although the present invention has been described with reference to various embodiments, those skilled in the art will recognize that changes may be made in form and detail without departing from the spirit and scope of the invention. As such, it is intended that the foregoing detailed description be regarded as illustrative rather than limiting and that it is the appended claims, including all equivalents thereof, which are intended to define the scope of the invention.

We claim:

1. A topical viscoelastic fluid modifying composition for topical application to the skin and hair in the perianal and/or labial areas comprising at least one viscoelastant material, an anti-adherent material, a skin conditioning agent, a structuring agent, and a rheology modifier,
   wherein the anti-adherent material is selected from the group consisting of fucans, inulin, sulphated exopolysaccharides, and combinations thereof;
   wherein the viscoelastant material comprises a material selected from the group consisting of linked enzymes, alkyl polyglycosides having 8-10 carbon atoms in the alkyl chain, dextrans, dextran derivatives, and combinations thereof;
   wherein the skin conditioning agent comprises an emollient selected from the group consisting of vegetable oils, partially hydrogenated vegetable oils, organo-siloxanes, silicone elastomers, and combinations thereof;
   wherein the structuring agent is selected from the group consisting of synthetic beeswax, stearyl trimethicone, candelilla wax, carnauba, ceresin, cetyl esters, behenyl benzoate, hydrogenated jojoba oil, hydrogenated jojoba wax, microcrystalline wax, hydrogenated microcrystalline wax, jojoba esters, lanolin wax, ozokerite parrafin, rice bran wax, synthetic candelilla wax, synthetic carnuba wax, synthetic jojoba wax, ethylene-alpha olefin copolymers, ethylene homopolymers, $C_{18}$-$C_{45}$ olefins, poly alpha olefins, and combinations thereof; and
   wherein the rheology modifier is selected from the group consisting of combinations of alpha-olefins and styrene or polyethylene alone or in combination with mineral oil or petrolatum, di-functional alpha-olefins and styrene alone or in combination with mineral oil or petrolatum, combinations of alpha olefins and isobutene, ethylene/propylene/styrene copolymers alone or in combination with mineral oil or petrolatum, butylene/ethylene/styrene copolymers alone or in combination with mineral oil or petrolatum, ethylene/vinyl acetate copolymers, polyethylene polyisobutylenes, polyisobutenes, polyisobutylene, dextrin palmitate, dextrin palmitate ethylhexanoate, stearoyl inulin, stearalkonium bentonite, stearalkonium hectorite, styrene/butadiene/styrene copolymers, styrene/isoprene/styrene copolymers, styrene-ethylene/butylene-styrene copolymers, styrene-ethylene/propylene-styrene copolymers, (styrene-butadiene) n polymers, (styrene-isoprene) n polymers, styrene-butadiene copolymers, styrene-ethylene/propylene copolymers, and combinations thereof.

2. The composition of claim 1, wherein the composition comprises between about 0.01% to about 25% by weight of the viscoelastant material and between about 0.01% to about 25% by weight of an anti-adherent material.

3. The composition of claim 1, wherein the skin conditioning agent is present in an amount from about 20% to about 90% by weight of the total composition; the structuring agent, when present, is present in an amount from about 10% to about 70% by weight of the total composition; and the rheology modifier, when present, is present in an amount from about 1% to about 25% by weight of the total composition.

4. The composition of claim 3, wherein the skin conditioning agent is present in an amount from about 30% to about 85% by weight of the total composition; the structuring agent, when present, is present in an amount from about 20% to about 65% by weight of the total composition; and the rheology modifier, when present, is present in an amount from about 2% to about 20% by weight of the total composition.

5. The composition of claim 4, wherein the viscoelastant material comprises about between 0.05% to about 10% by weight of the total composition and the anti-adherent material between 0.05% to about 10% by weight of the total composition.

6. The composition of claim 1, in the form of a spray, a solid stick composition, a foam, a wash, a cream, an ointment, a salve, a gel or a lotion.

7. A wet or dry wipe comprising a base substrate and the composition of claim 1.

8. The wet or dry wipe of claim 7, wherein the wipe is in the form of a glove or mitt.

9. A wrapper component for an absorbent article comprising an interior surface and an exterior surface, wherein the interior surface comprises the composition of claim 1.

10. An absorbent product comprising an absorbent article and the composition of claim 1, wherein the composition is provided on absorbent article, or co-packed with the absorbent article.

* * * * *